United States Patent
V. K. George et al.

(10) Patent No.: US 9,877,993 B2
(45) Date of Patent: Jan. 30, 2018

(54) COMPOSITION FOR COGNITIVE AND COSMETIC PURPOSES

(71) Applicant: BIOTROPICS MALAYSIA BERHAD, Shah Alam, Selangor (MY)

(72) Inventors: Annie George V. K. George, Selangor (MY); Kar Ming Yee, Kuala Lumpur (MY)

(73) Assignee: BIOTROPICS MALAYSIA BERHAD, Shah Alam, Selangor (MY)

( * ) Notice: Subject to any disclaimer, the term of this patent is extended or adjusted under 35 U.S.C. 154(b) by 318 days.

(21) Appl. No.: 14/424,180

(22) PCT Filed: Feb. 26, 2013

(86) PCT No.: PCT/MY2013/000033
§ 371 (c)(1),
(2) Date: Feb. 26, 2015

(87) PCT Pub. No.: WO2014/035233
PCT Pub. Date: Mar. 6, 2014

(65) Prior Publication Data
US 2015/0320821 A1    Nov. 12, 2015

(30) Foreign Application Priority Data
Aug. 29, 2012  (MY) .......................... PI 2012003882

(51) Int. Cl.
| | |
|---|---|
| *A61K 36/70* | (2006.01) |
| *A61K 36/704* | (2006.01) |
| *A61K 31/352* | (2006.01) |
| *A61K 31/7048* | (2006.01) |
| *A61K 8/60* | (2006.01) |
| *A61K 8/49* | (2006.01) |
| *A61Q 19/00* | (2006.01) |
| *A61Q 19/08* | (2006.01) |
| *A61K 8/97* | (2017.01) |

(52) U.S. Cl.
CPC ............ *A61K 36/704* (2013.01); *A61K 8/498* (2013.01); *A61K 8/602* (2013.01); *A61K 8/97* (2013.01); *A61K 31/352* (2013.01); *A61K 31/7048* (2013.01); *A61Q 19/00* (2013.01); *A61Q 19/08* (2013.01); *A61K 2800/522* (2013.01); *A61K 2800/84* (2013.01)

(58) Field of Classification Search
CPC ..................................................... A61K 36/70
USPC .......................................................... 424/774
See application file for complete search history.

(56) References Cited

U.S. PATENT DOCUMENTS

2012/0082737 A1    4/2012  Florence et al.

OTHER PUBLICATIONS

Hussain et al. "Cytotoxicity and phytotoxicity of some selected medicinal plants of the family Polygonaceae", African Journal of Biotechnology vol. 9 (5), pp. 770-774, Feb. 1, 2010.*
Vimala et al. "Aantioxidant Evaluation in Malaysian Medicinal Plant: Persicaria minor (Huds.) Leaf", Dec. 2011.*
Vimala, S. et al "Antioxdant evaluation in malaysian medicinal plant: Persicar minor (huds) leaf", Science Journal of Medicine and Clincal Trials, Jan. 1, 2012, vol. 2012, pp. 9-16.
Smolarz, Helena D., "Flavonoids from *Polygonum lapathifolium* ssp. tomentosum", Pharmaceutical Biology, Aug. 2002, vol. 40, No. 5, pp. 390-394.
Mantegna, Stefano et al., "A one-pot ultrasound-assisted water extraction/cyclodextrin encapsulation of resveratrol from Polygonum cuspidatum", Food Chemistry Feb. 1, 2012, vol. 130, No. 3, pp. 746-750.
Qdar, Suhailah Wasman et al. "Potential bioactive property of Polygonum minus huds (kesum) review" Scientific Research and Essays, Jan. 16, 2012, vol. 7, No. 2, pp. 90-93.

* cited by examiner

*Primary Examiner* — Christopher R Tate
*Assistant Examiner* — Deborah A Davis
(74) *Attorney, Agent, or Firm* — R. Neil Sudol; Henry D. Coleman

(57) ABSTRACT

The present invention relates to a composition containing an extract from the *Polygonum minus* for cognition and cosmetic purposes. The extract of *Polygonum minus* includes quercetin-3-glucuronide and quercitrin. Extract of *Polygonum minus* is provided in an amount effective to reduce oxidative damage. A process for isolation of an active extract from *Polygonum minus* includes the steps of a) subjecting the *Polygonum minus* including aerial parts of the plant to solvent extraction preferably with a material solvent ratio of 1:10-20 by percolation at a temperature range of 70-105° C. preferably 80° C. to obtain the extract; and b) filtering the extract obtained from step (a) followed by concentration and drying involving freeze drying, spray drying or vacuum belt drying to obtain therefrom the dry extract powder.

7 Claims, 8 Drawing Sheets

COMPOSITION FOR COGNITIVE AND COSMETIC PURPOSES

FIELD OF THE INVENTION

The present invention relates to a composition comprising an extract of *Polygonum minus*.

BACKGROUND OF INVENTION

*Polygonum minus* from the family Polygonaceae is locally known in Malaysia as kesum or laksa leaf. It is a local medicinal plant commonly consumed as ulam for preventive health care. The plant leaves are aromatic and is popularly used as an ingredient in Malaysian delicacies such as laksa (spicy noodle dish), kerabu (fried herbal rice), tom yam (spicy tangy soup) and asam pedas (spicy tamarind curry). The leaves are often sliced and sprinkled for its strong aroma and flavouring. In the Malaysian Traditional Medicine System, the decoction of the kesum fresh leaves is consumed for indigestion, constipation and as a remedy for stomach disorders and pain (Vimala S., Ilham, M. A., Rashih A. A. and Rohana S. (2003). Nature's Choice to Wellness: Antioxidant Vegetables/Ulam. Siri Alam and Rimba 7. Forest Research Institute Malaysia (FRIM), Pp 131).

Skin is subject to abuse by many extrinsic (environmental) factors as well as intrinsic factors. As skin ages, there is an increase in oxidative stress, an increase in inflammation, a decrease in collagen levels, overexpression of the enzyme MMP (Peptidase, Matrix Metalloproteinase-1), an increase in protein glycation, and an increase in mitochondrial decay and hence the oxidative damage.

There are currently numerous compositions in the market for such prevention and/or treatment. There are many combinations of different ingredients in cosmetics, such as antioxidants, enzymes, phytoestrogens, emollients, humectants, and the like. Their ability to protect the skin varies with the composition and its ingredients and hence there still remains a need for an effective formulation for both topical and/or systemic use harnessed from natural renewable botanical materials that can be used, without a prescription, to treat the effects of oxidation and other skin damage.

Further it also desirable in the art to explore for other characteristic attributes of the natural renewable material isolated, as they can be easily used having minimal or no side effects on mankind as compared to the synthetic molecules clinically tried and tested thereby imposing severe concerns to human health and environment.

It is relevant to mention that it is usually extremely difficult to provide for an effective skin care agent possessing both anti-oxidant activities by way of reactive oxygen scavenging (ROS) property in combination with anti-collagenase activity inhibiting the enzymes responsible for the breakdown of collagen. In the backdrop of the above existing challenge in the related art, it has been surprisingly found by way of the present invention that the extract of *Polygonum minus* also known as *Persicaria minor* meets the much desired criteria of a superior skin care cosmetic and/or pharmaceutical agent and/or compositions derived out of the same having skin benefiting attributes by way of dual anti-oxidant activity and anti-collagenase activity with a potential to prevent the breakdown of collagen to thus favour anti-wrinkling/anti-aging as well as protection of the living cells against oxidative damage due to its anti-oxidation characteristics.

SUMMARY OF INVENTION

The present invention is related to a composition containing an extract from the *Polygonum minus* for cognition and cosmetic purposes. The method of obtaining the said extract from the *Polygonum minus* is also disclosed.

In another preferred embodiment, the composition contains extract of *Polygonum minus* comprise actives selected from quercetin-3-glucuronide and quercitrin.

In another preferred embodiment, the composition contains selectively quercetin-3-glucuronide in amounts of 0.2 to 1.0% by weight sourced as extract of *Polygonum minus* and quercitrin in amounts of 0.1 to 0.5% by weight sourced as extract of *Polygonum minus*.

In another preferred embodiment, wherein the amount of said extract of *Polygonum minus* is selected based on its having efficacy in prevention of oxidative damage demonstrated in a Cell-based Antioxidant Protection in an Erythrocyte model (CAP-e assay) equivalent to 55 times of Gallic acid.

In another preferred embodiment, there is provided a process for isolation of an active extract from *Polygonum minus* comprising the steps of a) subjecting the said *Polygonum minus* including aerial parts of the plant including stem and/or leaves to solvent extraction preferably with a material solvent ratio of 1:10-20 by percolation at a temperature range of 70-105° C. preferably 80° C. to obtain the extract; and b) filtering the extract obtained from step (a) above followed by concentration and drying involving freeze drying, spray drying or vacuum belt drying to obtain therefrom the dry extract powder.

BRIEF DESCRIPTION OF THE FIGURES

FIG. 8($b$) illustrates primary path length study with reference control; FIG. 8($c$) illustrates total path length study with scopolamine and ginkgo, scopolamine and *P. minus* (100 mg/kg), scopolamine and *Polygonum minus* (50 mg/kg), scopolamine and vehicle and FIG. 8($d$) illustrates total path length study with reference control.

FIG. 9($b$) illustrates primary error study with reference control; FIG. 9($c$) illustrates total error study with scopolamine and *ginkgo*, scopolamine and *Polygonum minus* (100 mg/kg), scopolamine and *Polygonum minus* (50 mg/kg), scopolamine and vehicle and FIG. 9($d$) illustrates total error study with reference control.

DETAILED DESCRIPTION OF THE INVENTION

The present invention is related to a composition containing an extract from the *Polygonum minus* for cognition and cosmetic purposes. The method of obtaining the said extract from the *Polygonum minus* is also disclosed. The details of the invention, its advantages are explained hereunder in greater detail in relation to the following non-limiting examples and accompanying figures. Hereinafter, this specification will describe the present invention according to the preferred embodiments of the present invention. However, the following example is to be understood that limiting the description to the preferred embodiments of the invention is merely to facilitate discussion of the present invention and it is envisioned that those skilled in the art may devise various modifications and equivalents without departing from the scope of the appended claims.

Figure 1:
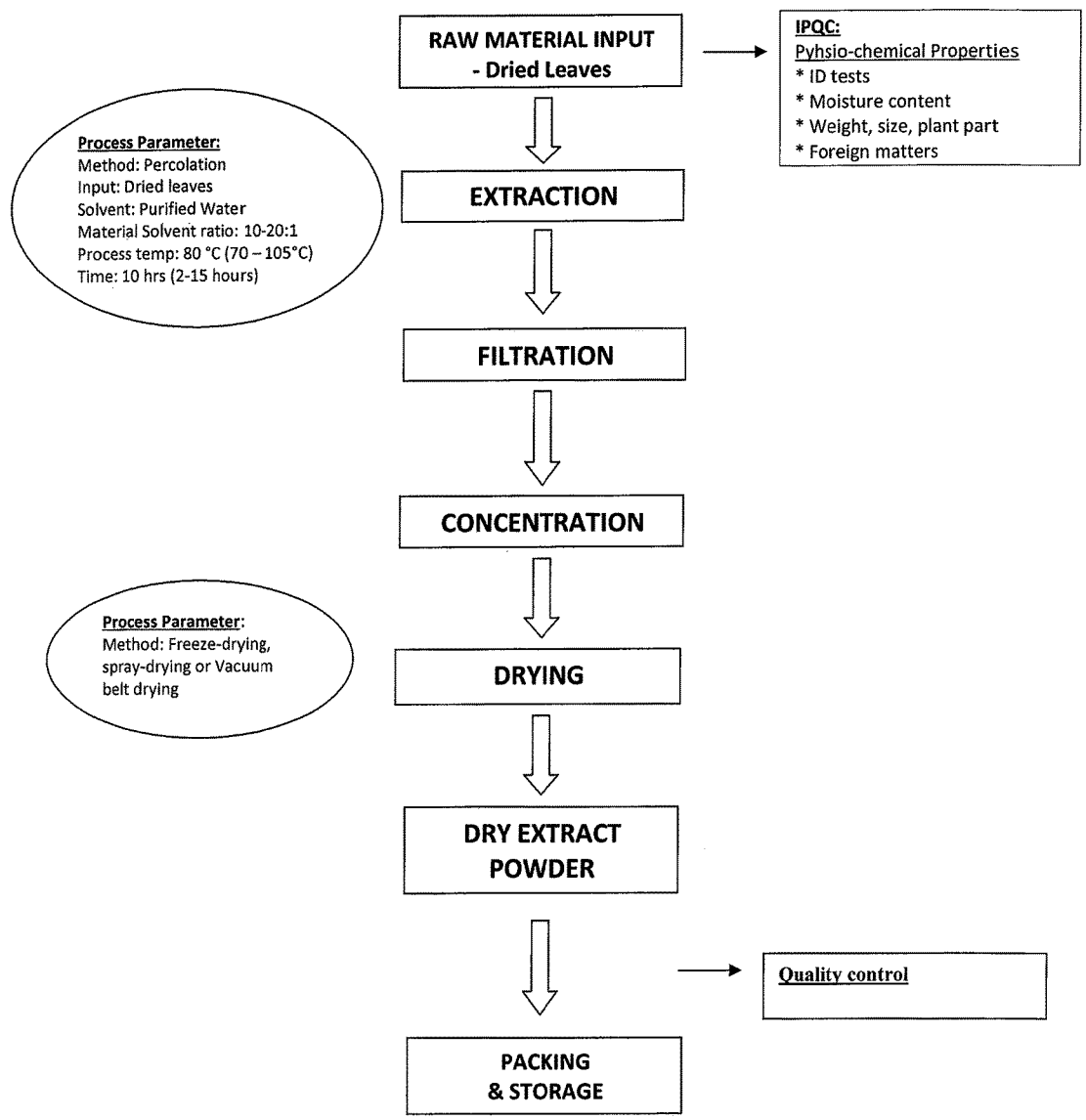
FIG. 1 illustrates the flow chart of providing the extract of *Polygonum minus*.

The aerial parts of the plants including stem and leaves is extracted using water and dried by oven drying with an extraction ratio of approximately 1:10. The raw material used is dried leaves with properties of 2 to 5 cm in size, not more than 10% in loss on drying, not more than 10% ash content, not more than 2% foreign matter, not more than $10^7$ total aerobic microbial count, not more than $10^5$ total yeast and mold count. The dried leaves were then subjected to the steps of percolation using purified water and extracted at a temperature in the range of 70-105° C. preferably at 80° C. to obtain the extract which is further filtered, concentrated, and dried using methods such as freeze drying, spray drying or vacuum belt drying to provide for a dry extract powder which is the packed and stored. After the drying step, the dry extract powder is package and stored at room temperature as per the flow sheet of FIG. 1.

The identification and quantification of actives in the extract and moisture content analysis of *Polygum minus* was studied and the results are provided hereunder:

The extract obtained is found to include actives quercetin-3-glucuronide and quercitrin as per the assay below:

HPLC Assay: Preparation of Sample Solution for HPLC Analysis
1. 100.0 mg of sample extract is accurately weighed in 5.0 mL volumetric flask and DMSO is added to volume.
2. The solution is then sonicated for 10 minutes at about 60° C., filtered with 0.20 m RC membrane filter and is used as test solution for HPLC analysis.

Mobile Phase Preparation
1. Channel A—1.0 mL of FA is added into 1000 mL of deionised water. The solution is filtered and degassed.
2. Channel B—1.0 mL of FA is added into 1000 mL of acetonitrile.

Chromatographic System (Agilent 1290 Infinity)

| Column | PhenomenexKinetex |
| --- | --- |
|  | (2.1 × 150 mm, 1.7 micron) |
| Temperature | 60.0° C. |
| Mobile Phase | Solvent A - 0.1% FA in Water |
|  | Solvent B - 0.1% FA in CAN |
| Flow rate | 0.400 mL/min (Gradient) |

| Gradient system | | |
| --- | --- | --- |
| Time (Min) | Solvent A (%) | Solvent B (%) |
| 0.00 | 89.0 | 11.0 |
| 18.00 | 89.0 | 11.0 |
| 20.00 | 5.0 | 95.0 |
| 23.00 | 5.0 | 95.0 |
| 25.00 | 89.0 | 95.0 |
| Wavelength | UV at 360 nm, Reference at 450 nm | |
| Run time | 25 minutes (with 5.0 min post run) | |
| Injection Volume | 2.0 µL | |
| Data Acquisition | 25 minutes | |

Figure 2A:
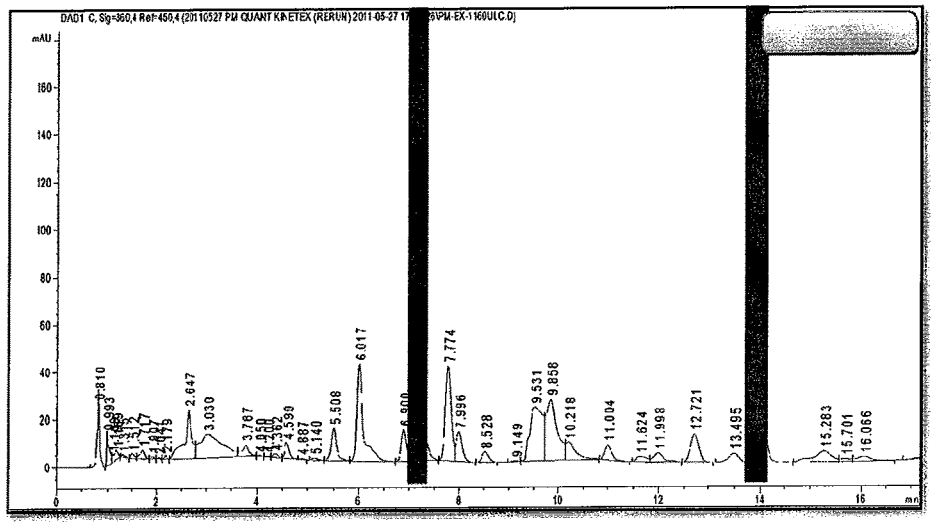
FIG. 2($a$) illustrates the results on HPLC histogram and FIG. 2($b$) illustrates the comparison of UV spectra of quercetin-3-glucuronide and quercitrin and the corresponding peaks in the extract.

With reference to FIG. 2(a), the highlighted region from left depicts the presence of quercetin-3-glucuronide and quercitrin respectively in the HPLC histogram. Further, quercetin-3-glucuronide and quercitin are quantified by % assay in the said final extract obtained from *Polygum minus* in Table 1 below.

Moisture Content Analysis

Moisture content of the sample extract is determined by using a moisture analyzer, in which about 0.5 to 0.6 g of powdered sample is transferred onto an aluminium pan and heated at 105° C. till a constant weight is obtained. The loss on drying (LOD) is determined by the percentage of weight loss during heating against the initial weight.

TABLE 1

HPLC Quantification by % Assay of Quercetin-3-glucuronide and Quercitin and moisture content analysis of the extract.

| Assay (w/w) % | |
| --- | --- |
| Quercetin-3-Glucuronide | 0.590818 |
| Quercitrin | 0.269141 |
| Moisture Content (%) | 5.76 |

Figure 2B:
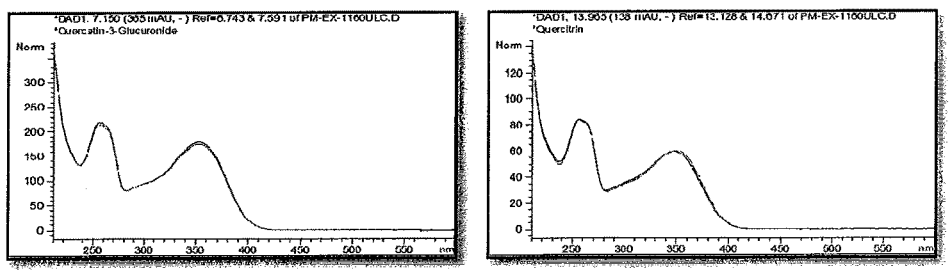

With reference to FIG. 2(b), comparison of retention time and UV spectra of quercetin-3-glucuronide and quercitrin with that of the sample extract of *Polygonum minus* showed the presence of both the compounds in said sample. Therefore, both quercetin-3-Glucuronide and quercitrin is positively identified in the sample extract of *Polygonum minus* as per HPLC studies above.

*Polygonum minus* extract was studied to reveal the cosmetic enhancing characteristics as per the results hereunder:

Antioxidant Activity of *Polygonum minus* Extract

The extract of *Polygonum minus* extract was tested for antioxidant activity using Oxygen Radical Absorbance Capacity (ORAC methods) which is shown to be very high with ORAC values (refer to tables below). Based on the tests conducted, the extract of *Polygonum minus* has preferred oxygen radical absorbency capacity (ORAC) values of between 11,000 micromole TE/gram to 36,000 micromole TE/gram with a preferred ORAC value of at least 16000 micromole TE/gram. The high ORAC values produced in *Polygonum minus* was further tested for the ability to protect living cells against oxidative damage, testing using e-CAP assay.

TABLE 2

The oxygen radical absorbency capacity (ORAC) obtained from a pilot freeze dried *Polygonum minus*.

| | Units (μmole TE/gram) |
|---|---|
| Antioxidant power against peroxyl radicals | 2591 |
| Antioxidant power against hydroxyl radicals | 8973 |
| Antioxidant power against peroxynitrite | 222 |
| Antioxidant power against super oxide anion | 4039 |
| Antioxidant power against singlet oxygen | 1139 |
| Total $ORAC_{FN}$ (Sum of Above) | 16964 |

TABLE 3

The oxygen radical absorbency capacity (ORAC) obtained from commercial freeze-dried *Polygonum minus*.

| | Units (μmole TE/gram) |
|---|---|
| Antioxidant power against peroxyl radicals | 1979 |
| Antioxidant power against hydroxyl radicals | 16060 |
| Antioxidant power against peroxynitrite | 200 |
| Antioxidant power against super oxide anion | 6995 |
| Antioxidant power against singlet oxygen | 1572 |
| Total $ORAC_{FN}$ (Sum of Above) | 26806 |

TABLE 4

The oxygen radical absorbency capacity (ORAC) obtained from pilot spray dried *Polygonum minus*.

| | Units (μmole TE/gram) |
|---|---|
| Antioxidant power against peroxyl radicals | 2393 |
| Antioxidant power against hydroxyl radicals | 23020 |
| Antioxidant power against peroxynitrite | 228 |
| Antioxidant power against super oxide anion | 8272 |
| Antioxidant power against singlet oxygen | 1611 |
| Total $ORAC_{FN}$ (Sum of Above) | 35524 |

TABLE 5

The oxygen radical absorbency capacity (ORAC) obtained from pilot freeze dried *Polygonum minus*.

| | Units (μmole TE/gram) |
|---|---|
| Antioxidant power against peroxyl radicals | 2013 |
| Antioxidant power against hydroxyl radicals | 19700 |
| Antioxidant power against peroxynitrite | 236 |
| Antioxidant power against super oxide anion | 10244 |
| Antioxidant power against singlet oxygen | 1925 |
| Total $ORAC_{FN}$ (Sum of Above) | 34118 |

TABLE 6

The oxygen radical absorbency capacity (ORAC) obtained from pilot vacuum belt dried *Polygonum minus* with maltodextrin as a carrier.

| | Units (μmole TE/gram) |
|---|---|
| Antioxidant power against peroxyl radicals | 784 |
| Antioxidant power against hydroxyl radicals | 6380 |
| Antioxidant power against peroxynitrite | 98 |
| Antioxidant power against super oxide anion | 3770 |
| Antioxidant power against singlet oxygen | 576 |
| Total $ORAC_{FN}$ (Sum of Above) | 11608 |

Cell-Based Antioxidant Protection in an Erythrocyte Model (CAP-e Assay)

The CAP-e assay (21) as a cell-based antioxidant protection assay using erythrocytes was developed to address the question of whether antioxidants in complex natural products enter the cytosol and contribute to the reduction of oxidative damage within the cell. The assay measures the effects in the cytosol only, as the reporter dye we use in the test is only functional after penetrating into the intracellular space (i.e. the cytosol) where it undergoes chemical modification, resulting in its retention within the cell. The assay allows for semiquantification specifically of those antioxidants that are capable of penetrating into live cells (Honzel et al., 2008. Comparison of Chemical and Cell-Based Antioxidant Methods for Evaluation of Foods and Natural Products: Generating Multifaceted Data by Parallel Testing Using Erythrocytes and Polymorphonuclear Cells. Journal of Agricultural and Food Chemistry).

For the test product, 0.5 g is mixed with 5 mL 0.9% saline at physiological pH. The test product is mixed by inversion and then vortexed. Solids are removed by centrifugation at 2400 rpm for 10 minutes. The supernatant of the products is removed and then filtered for use in the CAP-e assay. Serial dilutions are prepared from each filtered supernatant in 0.9% saline at physiological pH.

Red blood cells are treated in duplicate with serial dilutions of a test product. Samples of untreated red blood cells (negative controls) and samples of red blood cells treated with oxidizing agent but not with an antioxidant-containing test product (positive controls) are prepared in hexaplicate. The antioxidants not able to enter the cells are removed by centrifugation and aspiration of supernatant above the cell pellet.

The cells are exposed to oxidative damage by addition of the peroxyl free-radical generator AAPH. Using the indicator dye DCF-DA, which becomes fluorescent as a result of oxidative damage, the degree of antioxidant damage is recorded by measuring the fluorescence intensity of each test sample. The inhibition of oxidative damage is calculated as the reduced fluorescence intensity of product-treated cells, compared to cells treated only with the oxidizing agent. The CAP-e value reflects the $IC_{50}$ dose of the test products, i.e. the dose that provided 50% inhibition of oxidative damage. This is then compared to the $IC_{50}$ dose of the known antioxidant gallic acid.

Figure 3:
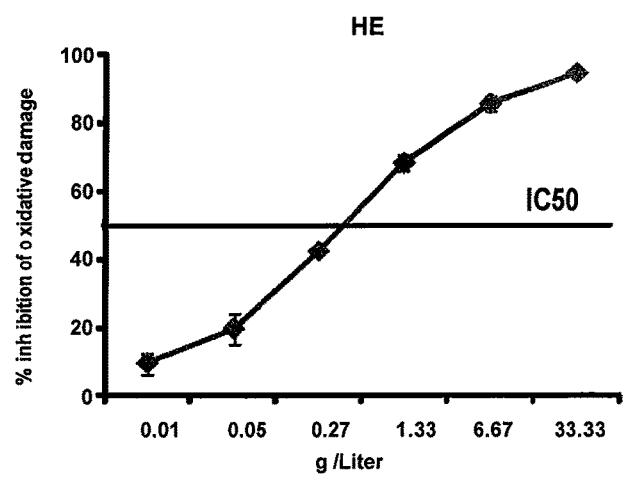
FIG. 3 illustrates the comparison of $IC_{50}$ dose of the extract to that of the known antioxidant gallic acid.

With reference to FIG. 3 wherein the point on the graph where the red $IC_{50}$ line intersects the curve reflects the $IC_{50}$ dose of the test product, i.e. the dose that provided 50% inhibition of oxidative damage. This $IC_{50}$ dose is compared to the $IC_{50}$ dose of the known antioxidant gallic acid (which is used as a control in the assay), resulting in a CAP-e value reported in gallic acid equivalent units. The antioxidant effect of the extract was tested for protection against free radicals in red blood cells. *Polygonum minus* extract demonstrated cell protective effects equivalent to 55 times (or possibly more than 55 times) of gallic acid, its' comparator hence proven to have reactive oxygen scavenging (ROS) activities.

Anti-Wrinkling Effect of *Polygonum minus* Extract

The extract was tested for anti-wrinkling effect using the anti-collagenase test and MMP-1 and MMP-13 in-vitro.

Collagenase Inhibition Bioassay In-Vitro

Collagen is the most abundant protein in vertebrates, and occurs in virtually every tissue. Collagen fibrils are the main components of the supporting tissue of connective tissues, bones cartilages, teeth and extracellular matrices of skin and blood vessels. There is a relationship between skin thickness and collagen content in men of all ages. A similar relationship exists among women over 60 years of age but it is less evident in younger women. In adult skin, the features of aging are closely related to the total collagen content, which in both sexes decreases with increasing age. Collagen is degraded by collagenase and thereby causing low collagen content in the skin. Thus, high collagenase activity of the skin can lead to wrinkling of the skin. Inhibitors of collagen should be helpful in controlling wrinkling formation in the skin. Of particular interest is the relationship between active collagenase and the pathology of rheumatoid arthritis. It has been suggested that the normally inhibited collagenase in articular structures may be activated therevy causing the characteristic tissue destruction in joints.

Solvents and reagents: EnzChek™gelatinase/Collagenase Assay kit (E12055, Molecular probes, Invitrogen, USA, Stored at −20° C.) containing: DQ gelatin from pigskin, Flourescein conjugate, 10× reaction buffer, 1,10 Phenanthroline monohydrate, Collagenase from *Clostridium histolyticum*.

2.5 mg of sample was prepared by dissolving it into 200 µl of DMSO and made up to 10 ml with 1× reaction buffer. Further dilutions were made as required. The enzymatic cleavage of DQ gelatin, Flourescein conjugate releases flourescent peptide. The increase in fluorescence is proportional to proteolytic activity. The digested product form DQ gelatin, Flourescein conjugate is excited with light at 490 nm and the emitted light at 520 nm is detected in a fluorometric plate reader.

Collagenase inhibition assay was carried out as per the kit insert of EnzChek™gelatinase/Collagenase Assay kit (E12055, Molecular probes, Invitrogen, USA). In brief, 80 µl of 1× reaction buffer/vehicle buffer/test solution/positive control of various concentrations, 100 µl of enzyme solution (0.1 units/ml), 20 µl of substrate solution (1 mg/ml) were added and mixed for 15 sec, incubated at 25° C. for 2 hours and read in a fluorescence microplate reader [Fluostar Optima, BMG Labtech, Germany] with the following parameters wherein it was excited at 490 nm, and the emission at 520 nm was recorded by the Costar 96 fluorometric plate reader.

A control reaction was carried out without the test samples respective sample blanking, control blanking and vehicle blanking were done (which contained all reagents except the enzymes). The percentage inhibition was calculated as follows:

$$\% \text{ inhibition} = \frac{AFU(\text{control}) - AFU(\text{test})}{AFU(\text{control}) \times 100} \times 100\%$$

where AFU=arbitrary fluorescence units and $IC_{50}$ was calculated using log-probit analysis.

| Tested material | Concentration tested | % inhibition | $IC_{50}$ (95% confidence interval) |
|---|---|---|---|
| 1,10-Phenanthroline monohydrate (positive control)(n = 2) | 12.5 µM<br>25 Mm<br>50 Mm<br>100 Mm | 0.00<br>11.60<br>40.81<br>88.00 | 53.19 µM<br>(48.23-58.89) |
| Pilot Freeze dried Extract of *P. Minus* | 2.5 µg/ml<br>5 µg/ml<br>10 µg/ml<br>25 µg/ml<br>50 µg/ml<br>100 µg/ml | 4.33<br>19.73<br>41.74<br>56.87<br>70.04<br>77.04 | 21.13 µg/ml<br>(17.55-25.70) |

Figure 4:
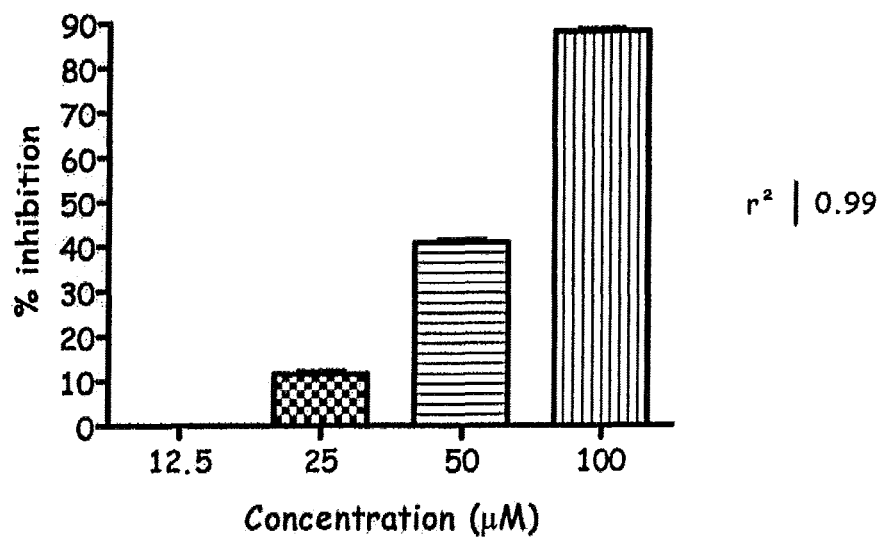
FIG. 4 illustrates the % inhibition of collagenase by the standard 1, 10 Phenanthroline monohydrate (control).
Figure 5:
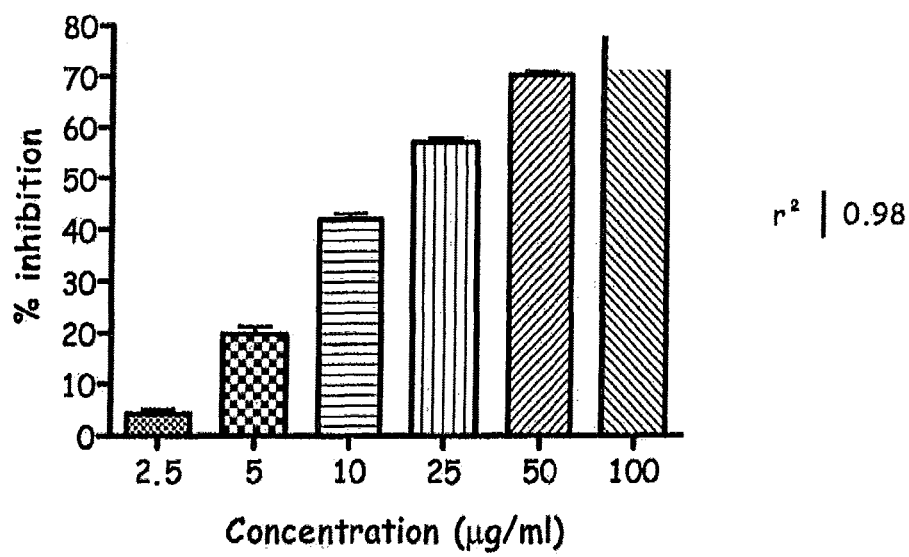
FIG. 5 illustrates the % inhibition of collagenase by the extract of *Polygonum minus*.

Table 7 above reveals that the concentration of the extract of *P. minus* at 21.13 µg/ml is the inhibitory concentration for 50% inhibition of collagenase activity. Further FIG. 4 and FIG. 5 indicates the % inhibition by the standard 1,10 Phenanthroline monohydrate and the extract of *Polygonum minus*.

| Peptidase, Matrix Metalloproteinase-1 (MMP-1) | Species | n= | Conc. | % inhibition | IC-CE |
|---|---|---|---|---|---|
| Pilot Freeze dried Extract of *P. minus* | hum | 2<br>2<br>2<br>2 | 50 mg/mL<br>30 mg/mL<br>10 mg/mL<br>5 mg/mL | 110<br>106<br>101<br>98 | <5 mg/mL |

The above Table 8 clearly reveals that the extract of *Polygonum minus* is effective at the levels of 5 mg/mL which concentration when increased up to the levels of 50 mg/mL does not much change the % inhibition and hence the levels of 5 mg/ml was considered to be the optimum level for maximum inhibition.

| Peptidase, Matrix Metalloproteinase-13 (MMP-13) | Species | n= | Conc. | % inhibition | IC-CE |
|---|---|---|---|---|---|
| Pilot Freeze dried Extract of *P. minus* | hum | 2<br>2<br>2 | 30 mg/mL<br>10 mg/mL<br>5 mg/mL | 102<br>101<br>100 | <5 mg/mL |

The above Table 9 clearly reveals that the extract of *Polygonum minus* is effective at the levels of 5 mg/mL which concentration when increased up to the levels of 30 mg/mL does not much change the % inhibition and hence the levels of 5 mg/ml was considered to be the optimum level for maximum inhibition at 100% of MMP-13. It is important to note that since MMP proteins of the matrix metalloproteinase (MMP) family are involved in the breakdown of collagen in normal physiological processes and hence preventing the breakdown of collagen by the extract of *Polygonum minus* slows down the aging effect as wrinkling is caused by the breakdown of collagen.

In addition to that, *Polygonum minus* extract was studied to reveal the cognition enhancing characteristics.

In Vitro Inhibitory Action of *Polygonum minus* Extract on Acetyl Cholinesterase and Monoamine Oxidase-A Acetylcholinesterase (AChE) is key enzyme in the nervous system of animals and considered to be the most important neurotransmitter involved in the regulation of cognitive functions. AChE inhibitors are among the key drugs approved by the FDA for management of Alzheimer's disease (AD). There are a number of studies linking decreased brain cholinesterase activity and improvement in memory. The extract was tested for inhibition of Acetyl Cholinesterase enzyme in vitro.

Monoamine oxidase (MAOs) also play in the inactivation of neurotransmitters, MAO dysfunction (too much or too little MAO activity) is responsible for a number of psychiatric and neurological disorders. For example, unusually high or low levels of MAOs in the body have been associated with depression, schizophrenia, substance abuse, attention deficit disorder, migraines, and irregular sexual maturation. Monoamine oxidase inhibitors are one of the major classes of drug prescribed for the treatment of depression, although they are often used as last-line treatment due to risk of the drug's interaction with diet or other drugs, and in fact, MAO-A inhibitors act as antidepressant and anti-anxiety agents.

| Target | Species | n= | Concentration in Ug/mL | % INH | IC-CE |
|---|---|---|---|---|---|
| Cholinesterase, Acetyl, ACES | hum | 2 | 100 | 68 | 40.5 Ug/mL |
| | | | 30 | 53 | |
| | | | 10 | 4 | |
| Monoamine Oxidase MAO-A | hum | 2 | 100 | 70 | 38.8 Ug/mL |
| | | | 30 | 44 | |
| | | | 10 | 23 | |
| Monoamine Oxidase MAO-B | hum | 2 | 100 | 47 | >100 Ug/mL |
| | | | 30 | 21 | |
| | | | 10 | 10 | |
| Adenosine AŽµ (Control) | hum | 2 | 100 | 10 | >100 Ug/mL |
| | | | 30 | 9 | |
| | | | 10 | 2 | |

‡ Partially soluble in in vitro test solvent.
* A standard error of the mean is presented where results are based on multiple, independent determinations.
hum = human Table 10 above thus clearly reveals the effect of the extract *Polygonum minus* towards the inhibition of Acetylcholinesterase and MAO-A wherein the inhibitory effects on both the said enzymes were found to be comparable while the said extract was not found to not play a prominent role towards the inhibition of Monoamine Oxidase MAO-B and Adenosine AŽµ.

Treatment with an Extract of *Polygonum minus* (*Persicaria minor*) on Scopolamine Induced Deficits in Learning and Memory The animals are placed on an elevated, open, circular platform. The animal is exposed to intense light, or to a loud noise. In response to this intense stimulation the animal searches for shelter and enters one of the holes around the platform. Although the device was originally designed to be used with rats, soon it experienced modifications in order to be used with mice as well. Indeed, the device has been considered appropriate for this species because of its ability to find and escape through small holes.

Scopolamine, a muscarinic cholinergic antagonist, is known to cause impairments in Barnes maze testing. These impairments can be reversed by increasing cholinergic tone by the administration of cholinesterase inhibitors such as donepezil. In the present study scopolamine treatment induced deficits during the early part of the acquisition (learning) phase of the Barnes maze and probe trial was carried out.

The scopolamine induced deficits in learning were evidenced by the increase in both total and primary errors, total and primary latency and total and primary path length. The Barnes mazes testing involves the parameters as set forth below.

Primary Path Length (cm): The distance moved by the subject before first contact with the escape hole. First contact is defined as the point of the nose touching the escape hole.

Total Path Length (cm): The distance moved by the subject before completing the task. Completion of task is defined as the entering of the subject into escape box. This ends the trial.

Primary Errors: The count of the number of errors made by the subject before first contact with the escape hole. Any contact of the nose point to a non-escape hole is considered as an error. Multiple contacts to the same non-escape hole are counted as multiple errors under this context.

Total Errors: The count of the number of errors made by the subject throughout the trial. Any contact of the nose point to a non-escape hole is considered as an error. Multiple contacts to the same non-escape hole are counted as multiple errors under this context.

Primary Latency (sec): The latency to the first contact with the escape hole by the nose point of the subject.

Total Latency (sec): The latency for subject to complete the task. Completion of task is defined as the entering of the subject into escape box, which ends the trial.

(i) Test Article

The test articles, propriety *Polygonum minus* extract and commercially available *Ginkgo biloba* extract (comparator extract) were used in this study. These extracts were prepared and stored for the project to the supplier's specifications. The doses of the extract chosen for the study were identified by the supplier A 30× stock suspension was prepared every week for each article. This was aliquot into batches which were then stored at 4° C. throughout the week. The stock suspension was diluted with ultra-pure water to working concentration every day before the dosing, and discarded after the dosing. Oral gavage needles were filled with the required amounts of suspension. Care was taken to ensure the even distribution of particles by vortex-mixing the suspensions before preparation in individual syringes, and also by syringe-mixing the diluted test article. The dose and time of scopolamine administration has been previously shown to produce deficits in spatial navigation tasks in rodents. The dose was increased from the initially reported 0.3 mg/kg to 0.5 mg/kg, as the higher dose would produce a more reliable deficit.

(ii) Control Article

Vehicle control was used as per protocol in Tables 11 and 12 below.

| CONTROL & TEST ARTICLES USED | | | | |
|---|---|---|---|---|
| Route | Name | Code Number | Dose | Source |
| p.o. (oral gavage) | Ultra-pure water | N.A | N.A | Cerca Insights |
| | Ginkgo biloba | DM-0063 | 50 mg/kg | Biotropics |
| | P. minus | DM-0064 (P11/RE049/C) | 50 mg/kg (Low Dose) 100 mg/kg (High Dose) | Biotropics |
| i.p. | 0.9% Saline | N.A | N.A | Cerca Insights |
| | Scopolamine | DM-0021 | 0.5 mg/kg | Sigma |
| | Donepezil | DM-0035 | 1 mg/kg | International Laboratory Company |

| ARM DESCRIPTION | | | | |
|---|---|---|---|---|
| Arm | Day 1-14 | Day 15-19 | Expression | Category |
| 1. Treatment Control | a. Vehicle by Oral Gavage | a. Vehicle by Oral Gavage<br>b. Vehicle i.p. 30 min prior<br>c. Vehicle i.p. 25 min prior | Veh/<br>Veh, Veh | Control |
| 2. Scopolamine Control | a. Vehicle by Oral Gavage | a. Vehicle by Oral Gavage<br>b. Scopolamine i.p. 30 min prior<br>c. Vehicle i.p. 25 min prior | Veh/<br>Sco, Veh | |
| 3. Reference Control | a. Vehicle by Oral Gavage | a. Vehicle by Oral Gavage<br>b. Scopolamine i.p. 30 min prior<br>c. donepezil i.p. 25 min prior | Veh/Sco,<br>Don | |
| 4. Comparator | a. *Ginkgo* by Oral Gavage | a. *Ginkgo* by Oral Gavage<br>b. Scopolamine i.p. 30 min prior<br>c. Vehicle i.p. 25 min prior | Gink<br>50 mg/kg/<br>Sco, Veh | Testing |
| 5. Test Dose 1 | a. Product Low Dose by Oral Gavage | a. Dose 1 by Oral Gavage<br>b. Scopolamine i.p. 30 min prior<br>c. Vehicle i.p. 25 min prior | P. min<br>50 mg/kg/<br>Sco, Veh | |
| 6. Test Dose 2 | a. Product High Dose by Oral Gavage | a. Dose 2 by Oral Gavage<br>b. Scopolamine i.p. 30 min prior<br>c. Vehicle i.p. 25 min prior | P. min<br>100 mg/kg/<br>Sco, eh | |

(iii) Animals 2-6 month-old male C57BL/6 mice (20-25 g), (n=12 to 14) were supplied by BioLASCO (Taiwan). They were housed in an IVC system (Allentown, USA) under a 12/12-h light/dark (200-300 Lux) cycle (lights on 07:00 h) with free access to food (Labdiet, formulated laboratory chow) and water and humidity keep between 50%-70%. The total animals used for each treatment are shown in the Table 13 below (subjects used for each arm in the experiment).

| Treatment groups | |
|---|---|
| Treatment | N |
| 1. Treatment Control (Vehicle/Saline, Vehicle) | 13 |
| 2. Scopolamine Control (Vehicle/Scopolamine, Vehicle) | 12 |
| 3. Reference Control (Vehicle/Scopolamine, Donepezil) | 14 |
| 4. Comparator (*Ginkgo* 50 mg/kg/Scopolamine, Vehicle) | 13 |
| 5. Test Dose 1 (*Polygonum minus* 50 mg/kg/Scopolamine, Vehicle) | 14 |
| 6. Test Dose 2 (*Polygonum minus* 100 mg/kg/Scopolamine, Vehicle) | 13 |

Chronic treatment via p.o. was conducted with the TEST COMPOUNDS (test dose 1 and 2) as per Table 12 and Table 12 above and CONTROL ARTICLES (vehicle and *ginkgo*) continuously for 19 days. Dosing was given daily at 1800 hr. Compounds are administered orally using needle gavage (20G). Chronic treatment via i.p. was conducted with the CONTROL ARTICLES (vehicle, scopolamine and donepezil) continuously for 5 days during the Barnes maze test. Treatment was given daily to each subject 30 min prior the test. Compounds were administered i.p. using 27G needle.

(iv) Procedure

Barnes maze assessment took 5 days for each subject, for 4 trials/day for 4 days (acquisition period) and probe trial taken 24 hours after the last acquisition trial. A pre-trial (adaptation period) was given prior the start of trial on day 1 and day 2. Tested subjects were administered with test compounds via i.p. with 27G needles, and returned back their home cages for 30 minutes. Barnes maze testing consisted of three phases, an adaptation period, an acquisition period and a probe trial. The detailed procedure is described in below section.

Experiment Timeline

Adaptation Period: The chamber was removed and the subject was allowed to explore the maze for 30 seconds and then gently guided to the escape hole. If the subject did not then enter the escape hole it was placed inside. The hole was then covered and the subject remained there for 3 minutes. The subject was then returned to its home cage and the platform cleaned with 70% ethanol.

Acquisition Period (Day 1-4):

In this period, the chamber was removed and the subject was allowed to explore the maze for 5 minutes and then gently guided to the escape hole. If the subject did not then enter the escape hole it was placed inside. The hole was then covered and the subject remained there for 1 minute. The subject was then returned to its home cage and the platform cleaned with 70% ethanol. The next trial was run after following an intertribal interval of two minutes.

During this period, the behavior of the experimental subjects was capture by video camera and recorded on the hard drive of a desktop PC. An analysis of these recordings was performed using EthoVision® XT tracking system for the automatic tracking and analysis of animal movement. The above discussed parameters were measured during the test and processed.

For each parameter, trials on each day averaged (4 trials for each subject in this study) and a mean performance value of every subject for the particular day was obtained. The mean of the four trials undertaken on any day by one subject is taken as one measure, so the n for the data points are based on the subject number alone. Data was further analyzed using two-way repeated measures ANOVA after the data underwent a normal distribution test, with Day as repeated measure factor within subjects and Group as between the subject's factor. Interaction of factors was examined as well. Post-hoc pairwise comparisons between groups using Tukey HSD test were carried out if significant effect was found. All graphs were plotted as mean±SE $\alpha$ level was set at 0.05 unless otherwise stated. Data analysis was performed using Sigma Plot statistical software.

Probe Trial (Day 5):

The probe trial was performed under the same environmental conditions as the acquisition trials.

Figure 6:
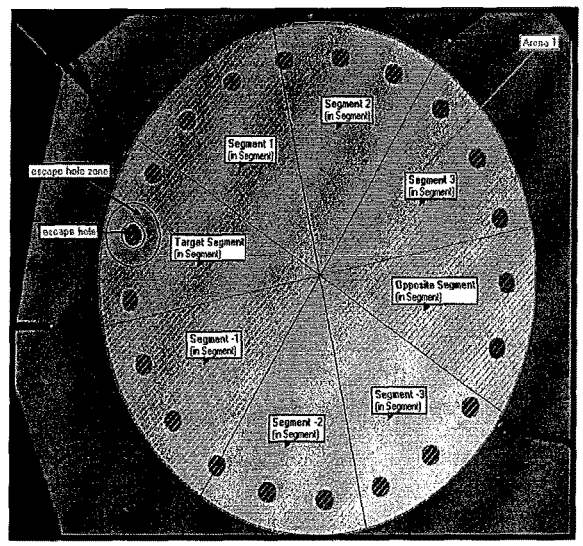
FIG. 6 illustrates schematic view of segments during probe trial of Barnes Maze test.

Duration in Segments (Sec):

The holes are closed by placing an identical white disc on the maze during probe trial. Subjects are given 90 sec to explore the maze. Arena was divided into 8 right equal segments (as shown in FIG. 6) and duration in each segment by the subject was measured using Ethovision video tracking software during the probe test. In the Barnes test the parameters were noted and are discussed hereunder.

Figure 7A:
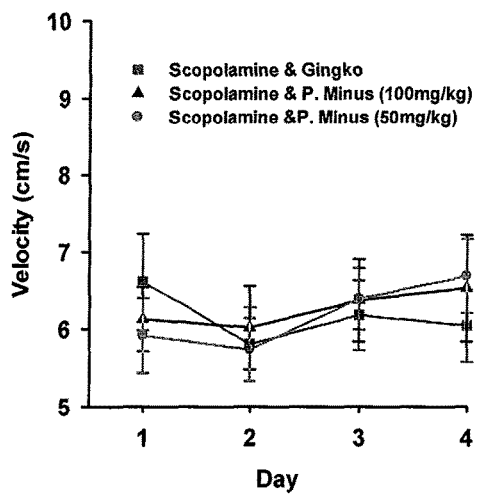
FIG. 7($a$) illustrates velocity in scopolamine treated mice that also received ginkgo and *Polygonum minus* treatment and FIG. 7($b$) illustrates velocity in scopolamine, scopolamine and donepezil and vehicle treated mice.
Figure 7B:
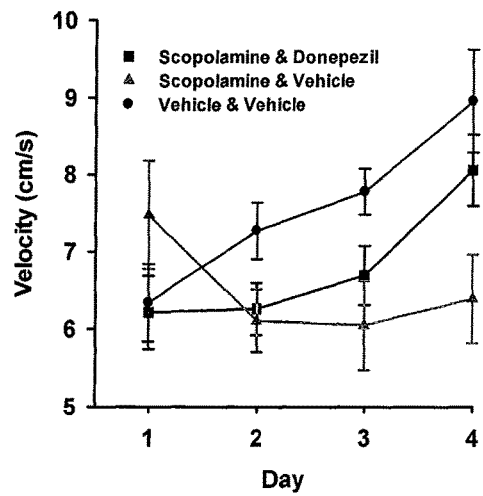
Figure 8A:
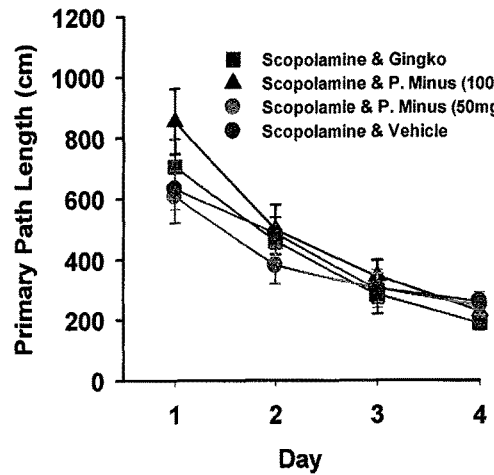
FIG. 8($a$) illustrates the primary path length study with scopolamine and ginkgo, scopolamine and *Polygonum minus* (100 mg/kg), scopolamine and *P. minus* (50 mg/kg), scopolamine and vehicle.
Figure 8B:
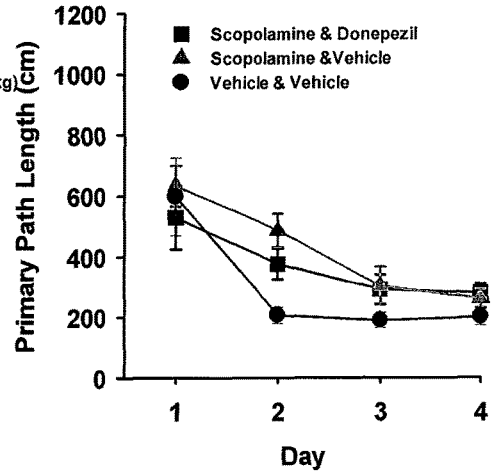
Figure 8C:
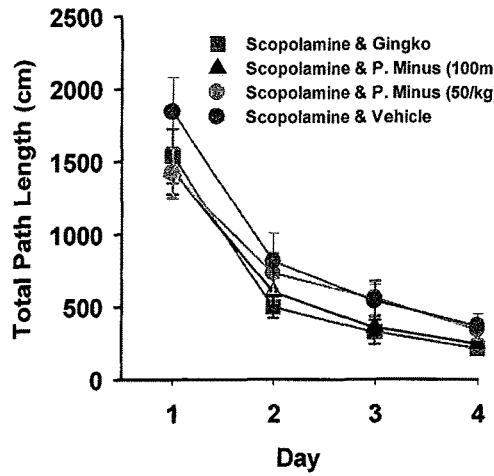
Figure 8D:
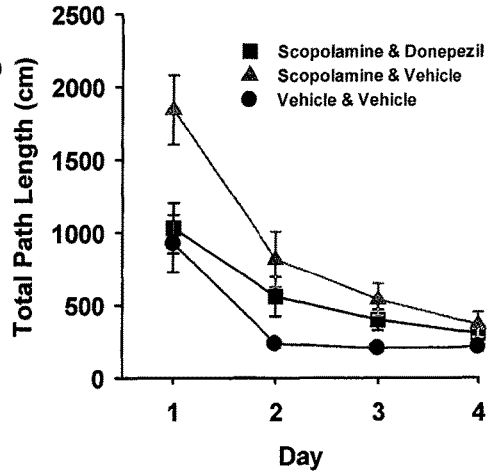
Figure 9A:
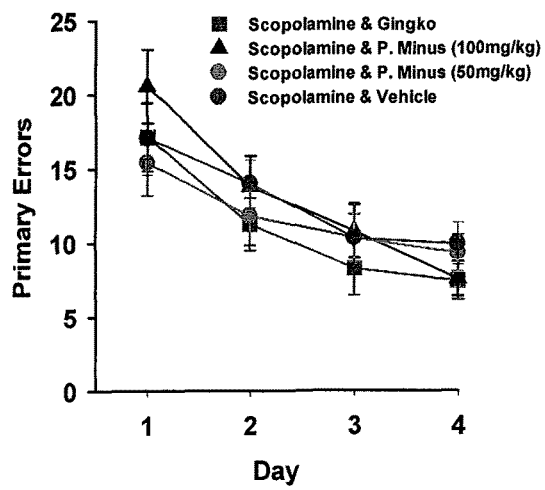
FIG. 9($a$) illustrates the primary error study with scopolamine and *ginkgo*, scopolamine and *Polygonum minus* (100 mg/kg), scopolamine and *Polygonum minus* (50 mg/kg), scopolamine and vehicle.
Figure 9B:
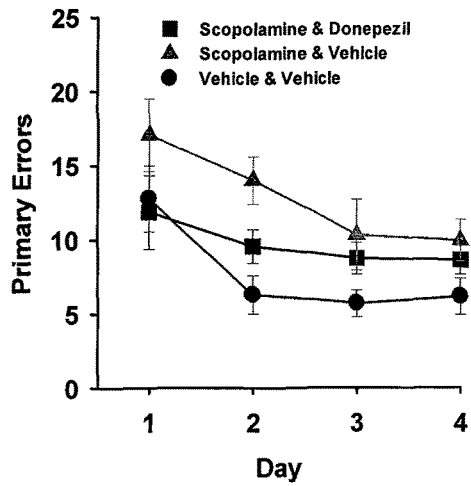
Figure 9C:
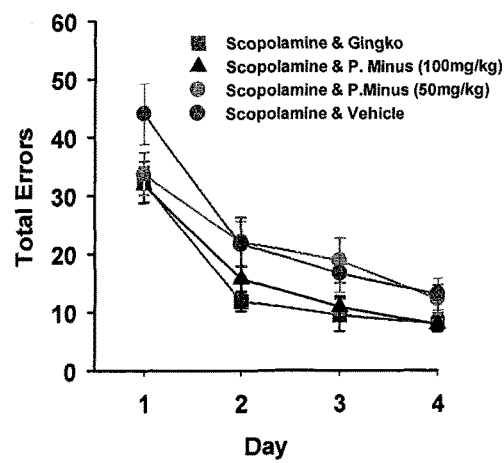
Figure 9D:
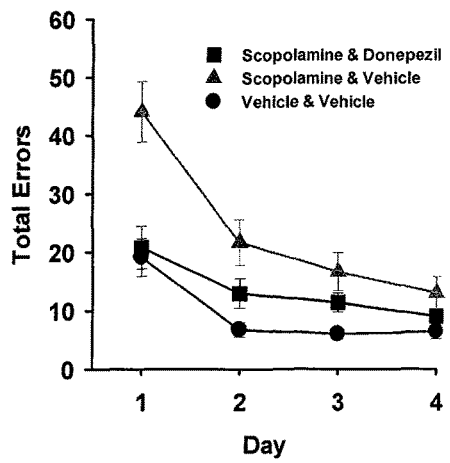
Figure 10A:
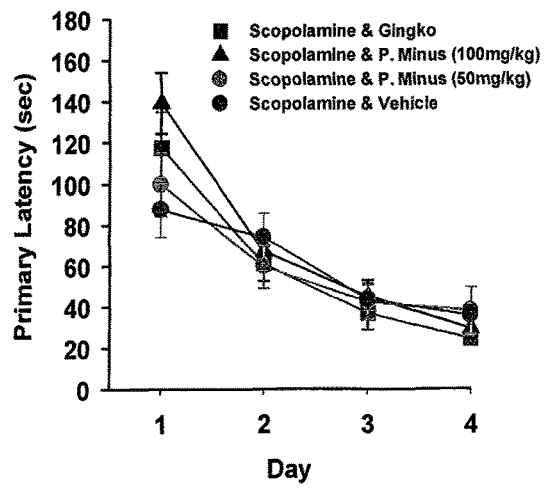
FIG. 10(a) illustrates the primary latency study with scopolamine and ginkgo, scopolamine and *Polygonum minus* (100 mg/kg), scopolamine and *Polygonum minus* (50 mg/kg), scopolamine and vehicle.
Figure 10B:
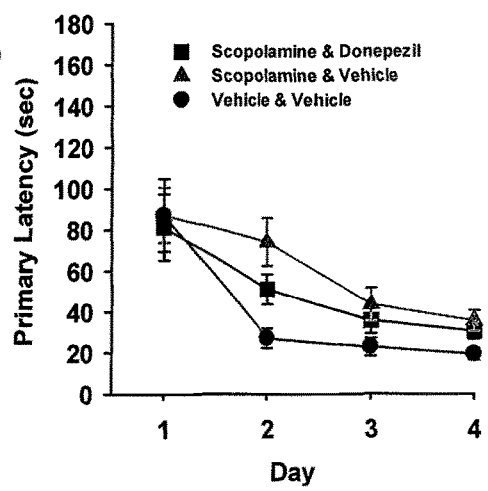
FIG. 10(b) illustrates primary latency study with reference control.
Figure 10C:
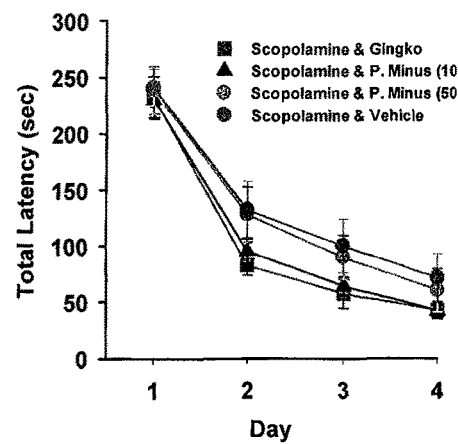
FIG. 10(c) illustrates total latency study with scopolamine and ginkgo, scopolamine and *Polygonum minus* (100 mg/kg), scopolamine and *Polygonum minus* (50 mg/kg), scopolamine and vehicle
Figure 10D:
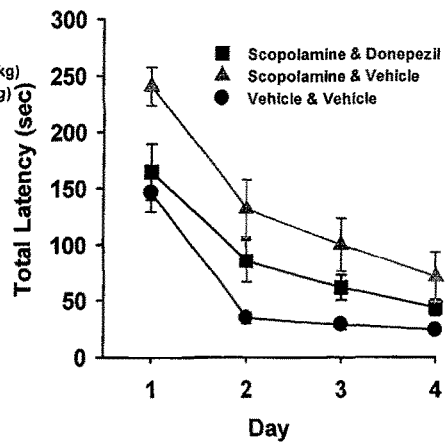
FIG. 10(d) illustrates total latency study with reference control.

Acquisition Period (Day 1-Day 4)
Velocity:

With reference to FIG. 7(a) and FIG. 7(b), two-way repeated measures ANOVA analysis revealed no significant effect of treatment on velocity and so the interpretation of the learning and memory measures are not confounded by stimulant or sedative effects of the test compounds.

Primary Path Length and Total Path Length:

With reference to FIG. 8(a), FIG. 8(b), FIG. 8(c) and FIG. 8(d), the figures show that scopolamine treatment decreased performance only on day two (for primary path length) and days one two and three (for total path length) when compared to the vehicle control treated group. This decrease in performance for total path length demonstrates a scopolamine induced deficit in learning in the Barnes maze. The scopolamine induced deficit was seen in the 50 mg/kg *Polygonum minus* treated mice; they showed a significant decrease in performance when compared to vehicle+vehicle treated mice on day two and three. This suggests that at this dose *Polygonum minus* treatment dose not reverse scopolamine induced deficits in the Barnes maze. However, the donepezil, *ginkgo* and the 100 mg/kg *Polygonum minus* treated mice did not show a scopolamine induced deficit. Their performance was not significantly different from vehicle+vehicle treated mice.

Primary Errors and Total Errors:

The results show that scopolamine induced a deficit in learning on day two (for primary errors) and on days one and two for total errors, when compared to the vehicle treated control mice. The deficits for total errors were not seen after treatment with *Polygonum minus* at 100 mg/kg, *ginkgo* or donepezil for days one and two, where there was a scopolamine induced deficit. These data suggest that the high dose of *Polygonum minus* can reverse scopolamine induced deficits in learning, as assessed by total errors. The lower dose of *Polygonum minus* appeared to reverse the scopolamine deficit on day two, as assessed by primary errors in FIG. 9(a), FIG. 9(b), FIG. 9(c) and FIG. 9(d).

Primary Latency and Total Latency:

These data show that when compared with vehicle control, scopolamine induces a deficit in learning. That is the scopolamine treated mice take longer to find the hole and escape from the maze. Mice treated with the high dose of *Polygonum minus* behave the same as the vehicle treated mice and do not show a scopolamine deficit in learning. A similar result is obtained with donepezil treatment and with *ginkgo* treatment as shown in FIG. 10 (a), FIG. 10(b), FIG. 10(c) and FIG. 10(d).

Figure 11:
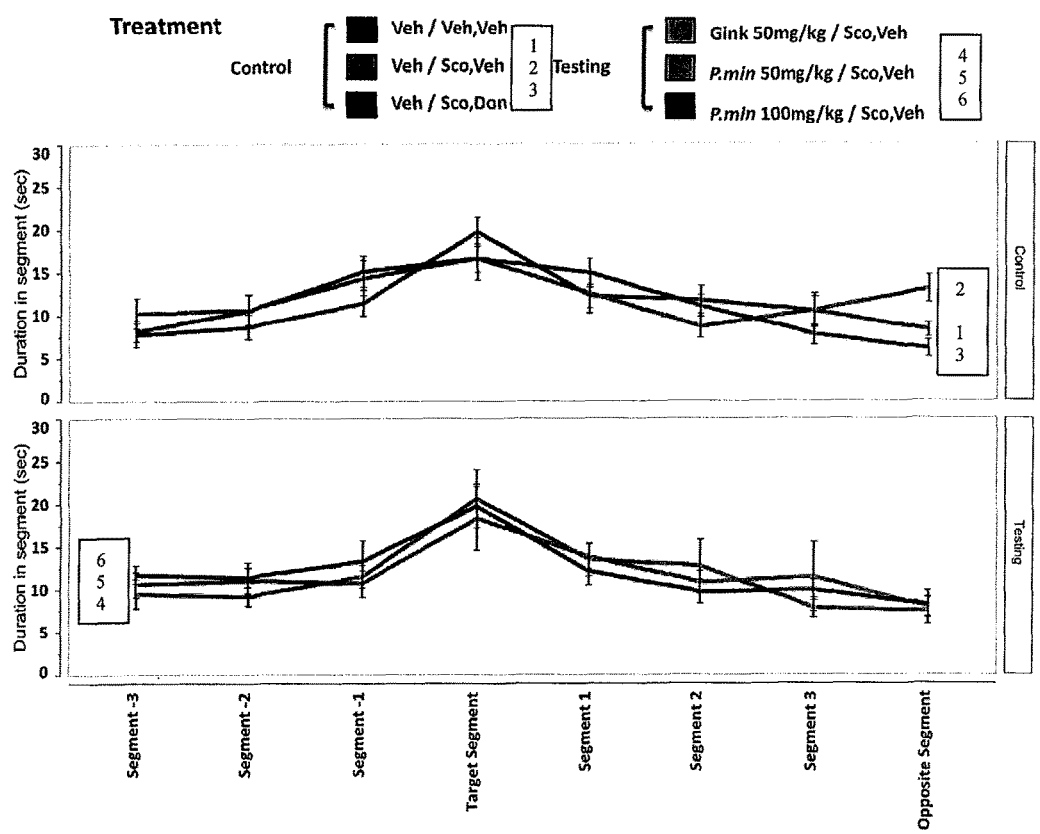
FIG. 11 illustrates the time spent in segments in scopolamine treated group and *Polygonum minus* treated group at 50 mg/kg and 100 mg/kg.

On probe trial (Day 5), there is no significant difference found on time spent in segments in scopolamine treated group and *Polygonum minus* treated group at 50 mg/kg. FIG. 10 (FIG. 11) shows that during the probe trial the mice perform the task but there is no escape hole. The mice are allowed to explore the maze and the time the mice stay in various areas on the maze is recorded. This 'probe' trial is used to assess memory. Mice treated with scopolamine did not show a preference for the 'target' segment of the maze—where, on the previous trials the escape hole was located. This suggests that scopolamine has induced a deficit in memory. This memory deficit was not reversed by the low dose of *Polygonum minus*, as these mice too, did not show a preference for the target segment. Both *ginkgo* and donepezil treatment reversed the scopolamine deficit—effects that have been reported by various laboratories. The high dose of *Polygonum minus* also reversed scopolamine induced memory deficits as the mice treated with *Polygonum minus* extract of 100 mg/kg spent a significant amount of time in the target segment.

In the present study scopolamine treatment induced deficits during the early part of the acquisition (learning) phase of the Barnes maze. The scopolamine induced deficits in learning were evidenced by the increase in both total and primary errors, total and primary latency and total and primary path length. Considering the learning curve, the impairment of scopolamine treated animals seemed most pronounced in the early in training, after which some constancy was reached between the treatment groups, this is best illustrated by the increased total path length in the scopolamine treated mice on days one, two and three, but not day four. These deficits were attenuated by the positive controls—donepezil and the *ginkgo* extract. Additionally the *Polygonum minus* at 100 mg/kg attenuated scopolamine induced deficits in the acquisition phase of the Barnes maze. The test compounds reversed scopolamine induced deficits in the retention (probe trial) aspect of the task. In the probe trial all the treatments except the low dose of 50 mg/kg of *Polygonum minus* attenuated scopolamine induced deficits. These deficits were described by no significant time spent in the target segment by the mice. The lack of effect of the low dose and the significant effect of the high dose would suggest that there was a dose dependent action of the extract.

The learning deficits of scopolamine were present early in the experiment and the results suggest that an extract of *Polygonum minus* can attenuate these scopolamine induced learning and memory deficits in mice. The present study used the Barnes maze which provides an assessment of spatial memory.

It is thus made possible by way of the technical advance of the present invention to provide an extract of *Polygonum minus* also known as *Persicaria minor*, with a potential of preventing the cells from oxidative damage in having high ORAC values of at least 16000 micromole TE/gram of said extract, which exhibits protective effect against wrinkling and aging by possessing a strong inhibitory effect towards MMP-1 (Peptidase, Matrix Metalloproteinase-1) and MMP-13 (Peptidase, Matrix Metalloproteinase-13) to thereby prevent the breakdown of collagen; and a benefit to cognition through improvement in memory and learning potentially via the anti-cholinesterase effect of the extract.

Thus, the water extract of *Polygonum minus* characterized by the presence of markers quercetin-3-glucuronide and quercitrin is remarkably found to be effective as cognitive enhancer and is potentially active towards the treatment of depression and anxiety by being a potential acetyl cholinesterase and monoamine oxidase-A enzyme inhibitor respectively.

The invention claimed is:

1. A method of treating deficits in learning and memory in a subject in need thereof, comprising a step of administering an effective amount of a composition to the subject to treat the deficits, wherein the composition comprises a therapeutically effective amount of a *Polygonum minus* extract, wherein the extract of *Polygonum minus* is comprised of quercetin-3-glucuronide and quercitrin, wherein the quercetin-3-glucuronide is in an amount of 0.2% to 1% by weight of the extract, and wherein the quercetin is in an amount of 0.1% to 0.5% by weight of the extract.

2. The method as claimed in claim 1 wherein the extract of *Polygonum minus* has oxygen radical absorbency capacity (ORAC) values of between 11,000 micromole TE/gram to 36,000 micromole TE/gram.

3. The method as claimed in claim 2 wherein the extract of *Polygonum minus* has an oxygen radical absorbency capacity (ORAC) value of at least 16000 micromole TE/gram.

4. The method as claimed in claim 1, wherein the quercetin-3-glucoronide is in an amount of 0.5% by weight of the extract.

5. The method as claimed in claim 1, wherein the quercetin-3-glucoronide is in an amount of 0.2% by weight of the extract.

6. The method as claimed in claim 1, wherein the composition is administered orally in combination with or without other agents.

7. The method as claimed in claim 1, wherein the therapeutically effective amount of the composition is 1 mg/kg body weight to 100 mg/kg body weight.

* * * * *